United States Patent
Eck et al.

(10) Patent No.: US 7,307,189 B2
(45) Date of Patent: *Dec. 11, 2007

(54) METHOD FOR DISCONTINUOUS PURIFICATION OF CRUDE ACRYLIC ACID BY MEANS OF CRYSTALLIZATION

(75) Inventors: Bernd Eck, Viernheim (DE); Dieter Baumann, Walldorf (DE); Joerg Heilek, Bammental (DE); Klaus Joachim Mueller-Engel, Stutensee (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 546 days.

This patent is subject to a terminal disclaimer.

(21) Appl. No.: 10/275,859

(22) PCT Filed: May 16, 2001

(86) PCT No.: PCT/EP01/05551

§ 371 (c)(1),
(2), (4) Date: Nov. 12, 2002

(87) PCT Pub. No.: WO01/92197

PCT Pub. Date: Dec. 6, 2001

(65) Prior Publication Data

US 2003/0149301 A1    Aug. 7, 2003

(30) Foreign Application Priority Data

May 29, 2000    (DE) .............................. 100 26 407

(51) Int. Cl.
*C07C 51/42*    (2006.01)

(52) U.S. Cl. ..................................................... 562/600
(58) Field of Classification Search ................ 562/512, 562/548, 600
See application file for complete search history.

(56) References Cited

U.S. PATENT DOCUMENTS

| 4,882,430 A | | 11/1989 | Neubauer et al. | |
| 5,817,865 A | * | 10/1998 | Machhammer et al. | 560/208 |
| 5,831,124 A | * | 11/1998 | Machhammer et al. | 562/600 |
| 6,541,665 B1 | * | 4/2003 | Bastiaensen et al. | 562/600 |
| 2003/0018214 A1 | * | 1/2003 | Decker et al. | 562/600 |

FOREIGN PATENT DOCUMENTS

| DE | 43 08 087 | | 9/1994 |
| DE | 195 08 558 | | 9/1996 |
| DE | 196 00 955 | | 7/1997 |
| DE | 198 29 477 | * | 1/2000 |
| EP | 0 373 728 | | 6/1990 |
| EP | 0 257 565 | | 1/1991 |
| EP | 0 293 224 | | 9/1992 |
| EP | 0 616 998 | | 5/1996 |

OTHER PUBLICATIONS

U.S. Appl. No. 09/719,572, filed Jan. 2, 2001, Allowed.
U.S. Appl. No. 10/275,859, filed Nov. 12, 2002, Pending.

* cited by examiner

*Primary Examiner*—Karl Puttlitz
(74) *Attorney, Agent, or Firm*—Oblon, Spivak, McClelland, Maier & Neustadt, P.C.

(57) ABSTRACT

Crude acrylic acid is purified batchwise by crystallization by a process which comprises at least one purification stage and at least one stripping stage and in which at least the first stripping stage is carried out in a different crystallizer from the first purification stage.

7 Claims, No Drawings

METHOD FOR DISCONTINUOUS PURIFICATION OF CRUDE ACRYLIC ACID BY MEANS OF CRYSTALLIZATION

BACKGROUND OF THE INVENTION

1. Field of the Invention

The present invention relates to a process for the batchwise purification of crude acrylic acid, which comprises at least one stripping stage and at least one purification stage.

2. Description of the Background

Acrylic acid is a key chemical which is used, for example, as such or in the form of its alkyl esters for the preparation of polymers produced by free radical polymerization.

Usually, acrylic acid is prepared by gas-phase oxidation of propene and/or propane under heterogeneous catalysis (cf. for example DE-A 19 508 558, EP-A 293 224, EP-A 257 565 and the literature cited in these publications).

The gas mixture leaving the gas-phase oxidation does not, of course, consist of pure acrylic acid but of a gas mixture which contains the latter and from which acrylic acid has to be isolated.

The various known methods for isolating acrylic acid from the product gas mixture of the gas-phase oxidation are summarized in, for example, DE-A 19 600 955.

A common feature of the known separation methods is that the desired acrylic acid is first isolated from the reaction gas mixture either by absorption using a solvent (cf. also DE-A 4 308 087) or by partial condensation. The resulting absorbate or condensate is then worked up, as a rule by distillation (with or without the addition of an azeotropic entraining agent) and/or extraction, to give an acrylic acid quality which usually contains, based on its weight, $\geq 95\%$ by weight, frequently $\geq 96\%$ by weight or $\geq 97\%$ by weight, often $\geq 98\%$ by weight, in some cases $\geq 99\%$ by weight and in some cases even $\geq 99.5\%$ by weight of acrylic acid.

Acrylic acids of the abovementioned qualities are all to be referred to in this publication very generally by the term crude acrylic acid. Typically, they contain at least one of the following impurities: water, acetic acid, propionic acid, low molecular weight aldehydes, such as acrolein, furfural or benzaldehyde, esters of acrylic acid and allyl alcohol, maleic anhydride, a process polymerization inhibitor, e.g. phenothiazine and/or N-oxyl radicals and diacrylic acid (the adduct formed by Michael addition of acrylic acid with itself when mixtures containing acrylic acid are left to stand).

When acrylic acid is used, for example for free radical polymerization purposes, the majority of the abovementioned impurities prove to be troublesome (for example, they produce discolorations of the resulting polymer or influence the induction time, i.e. the time until the beginning of the polymerization, in a disadvantageous manner).

A particularly undesirable impurity proves to be diacrylic acid. Although it generally undergoes free radical copolymerization, it does so with the disadvantage that it cleaves when the polymer is subjected to a thermal load and liberates monomeric acrylic acid, which cannot be tolerated particularly when the polymer is used in the hygiene sector (keyword: superabsorbers in babies' diapers; these polymers are partially neutralized polyacrylic acids obtained by free radical polymerization).

Usually, crude acrylic acid is therefore not used as such but only after further purification to give pure acrylic acid.

The literature (cf. e.g. EP-A 616 998) proposes carrying out the purification of crude acrylic acid to pure acrylic acid by batchwise crystallization. There, the initial crude acrylic acid is separated by the action of low temperatures, in a first crystallization step, into acrylic acid crystals having a higher purity than the initial crude acrylic acid and into a mother liquor having a lower purity than the initial crude acrylic acid. The crystallization can be carried out both statically (the melt is at rest during the crystallization, e.g. plate-type crystallizer or ribbed-tube crystallizer) and dynamically (the melt is agitated during the crystallization, e.g. falling-film crystallizer or tube with flow over the whole cross section). The resulting acrylic acid crystals are melted and, if required, further purified in one or more further crystallization steps carried out in succession.

To ensure that the yield is economical, the mother liquor obtained in the first crystallization step is also subjected to at least one further crystallization step. The crystallization steps in which the melt to be crystallized originates from the acrylic acid crystals obtained in the first crystallization step are generally referred to as purification stages. Likewise, the first crystallization step is referred to as the purification stage. In contrast, all crystallization steps in which the melt to be crystallized has originated from the mother liquor obtained in the first crystallization step are referred to as stripping stages.

This means that a batchwise purification of crude acrylic acid by crystallization usually comprises at least one purification stage and at least one stripping stage.

For the batchwise purification of crude acrylic acid, too, the prior art (e.g. EP-A 616 998) recommends carrying out both the one or more purification stages (i.e. including any additionally used purification stages) and at least the first stripping stage in one and the same crystallizer, i.e. in a single crystallizer. The disadvantage of this procedure is that those fractions of the initial crude acrylic acid which are not subjected to a crystallization in the crystallizer are temporarily stored in containers. During this temporary storage, however, diacrylic acid forms. In a subsequent crystallization stage, the diacrylic acid formed during the temporary storage is separated off, but the diacrylic acid separated off is equivalent to a lower yield of pure acrylic acid.

SUMMARY OF THE INVENTION

It is an object of the present invention to provide an improved process for the batchwise purification of crude acrylic acid by crystallization.

We have found that this object is achieved by a batchwise process for the purification of crude acrylic acid, comprising at least one purification stage and at least one stripping stage, wherein at least the first stripping stage is carried out in a different crystallizer from the first purification stage.

DETAILED DESCRIPTION OF THE PREFERRED EMBODIMENTS

The present invention is particularly important in that the amount of mother liquor remaining after the first purification stage is substantially smaller than the amount of initial crude acrylic acid to be purified by crystallization in the first purification stage.

Since, however, the dimensioning of the crystallizer used for the first purification stage (referred to below as crystallizer A) must necessarily be tailored to the amount of initial crude acrylic acid to be treated by crystallization at this stage, the crystallizer A is usually overdimensioned for further purification, by crystallization, of the mother liquor obtained in the first purification stage and it is for this reason that in practice, when only a single crystallizer is used for batchwise purification of initial crude acrylic acid by crystallization, a procedure is adopted in which a plurality of mother liquors obtained in successively performed first purifcation stages are collected until the amount of mother liquor originating from first purification stages and to be further purified by crystallization is appropriate to the dimension of the crystallizer A (otherwise the space-time yield of pure acrylic acid which is obtainable using crystallizer A is not fully satisfactory).

In the abovementioned case, the diacrylic acid formation due to the relatively long time required for temporary storage of mother liquor from first purification stages is particularly pronounced in said mother liquor.

It is therefore expedient according to the invention to use, for the first stripping stage, a crystallizer (referred to below as crystallizer B) which is designed for a smaller amount to be crystallized, which is only from 10 to 60, preferably from 20 to 50, particularly preferably from 20 to 40, very particularly from 25 to 35, % by volume of the amount of initial crude acrylic acid to be purified by crystallization in the first purification stage.

According to the invention, both the crystallizer A and the crystallizer B may be a dynamic or a static crystallizer. It is, of course, also possible for the crystallizer A to be a dynamic crystallizer and for the crystallizer B to be a static crystallizer (or vice versa).

It is preferable, according to the invention, if both the crystallizer A and the crystallizer B are dynamic crystallizers.

It is particularly expedient if both the crystallizer A and the crystallizer B are falling-film crystallizers, advantageously tubular falling-film crystallizers in both cases, as described in EP-A 616 998.

In this case, a tubular falling-film crystallizer B used according to the invention advantageously contains only from 10 to 60, preferably from 20 to 50, particularly preferably from 20 to 40, very particularly preferably from 25 to 35, % of the crystallization tubes contained in the tubular falling-film crystallizer A to be used according to the invention.

Moreover, the two or more crystallizers A and B to be used according to the invention can be operated in a manner known per se.

A pair of crystallizers A and B according to the invention is to be referred to as a crystallizer tandem for the purposes of this invention.

Finally, it should be noted that the novel process is used in an outstanding manner also when the amount of acrylic acid frozen out in the first purification stage is only up to 30% by weight of the initial crude acrylic acid used.

According to the invention, the crystallizer A can, of course, be used for further purification stages (second, third, etc.) and the crystallizer B for further stripping stages (second, third, etc.).

For an identical production capacity of pure acrylic acid, the novel process is always more advantageous with regard to the diacrylic acid waste than a process which uses only one crystallizer.

Its advantageousness is evident in particular when both more than one purification stage and more than one stripping stage are used.

We claim:

1. A process for the batchwise purification of crude acrylic acid by crystallization, consisting essentially of:
    at least one purification stage comprising a tubular falling film crystallizer A in which an amount of crude acrylic acid is subjected to crystallization and at least one stripping stage comprising a tubular falling film crystallizer B in which an amount of mother liquor produced in the at least one crystallizer A is subjected to crystallization, said crystallizer A being different from said crystallizer B, wherein, in at least the first stripping stage, mother liquor obtained from crystallization of crude acrylic acid in crystallizer A of the first purification stage is crystallized in crystallizer B and wherein each of the crystallizers A and B is comprised of crystallization tubes.

2. The process as claimed in claim 1, wherein the amount of mother liquor to be purified by crystallization in crystallizer B ranges from 10 to 60% by volume of the amount of crude acrylic acid subjected to crystallization in crystallizer A.

3. The process as claimed in claim 1, wherein the amount of said mother liquor obtained from the first purification stage is smaller than the amount of the crude acrylic acid crystallized in tubular falling-film crystallizer A of the first purification stage.

4. The process as claimed in claim 2, wherein the amount of mother liquor to be purified by crystallization in crystallizer B ranges from 20 to 50% by volume of the amount of crude acrylic acid subjected to crystallization in crystallizer A.

5. The process as claimed in claim 3, wherein the amount of said mother liquor to be purified in crystallizer B ranges from 20 to 40% by volume of the amount of crude acrylic acid to be purified in crystallizer A.

6. The process as claimed in claim 3, wherein the amount of acrylic acid that crystallizes in the first purification stage is up to 30% by weight of the quantity of initial crude acrylic acid placed in crystallizer A.

7. A process for the batchwise purification of crude acrylic acid by crystallization in an apparatus consisting of a tubular falling film crystallizer A and a separate and distinct tubular falling film crystallizer B, each of the crystallizers being comprised of crystallization tubes, comprising, in a batchwise manner:
    i) passing a volume of crude acrylic acid in an at least one first purification stage to said tubular falling film crystallizer A in which crystals of purified acrylic acid and a mother liquor form; and
    ii) passing substantially all of said mother liquor, which has a volume ranging from 10 to 60% of the volume amount of the crude acrylic acid that enters crystallizer A in step i), in a first stripping stage to said crystallizer B whose size is proportionately reduced relative to the size of crystallizer A to a degree that is commensurate with the 10 to 60% reduced volume of the mother liquor, thereby forming crystals of acrylic acid as a product in crystallizer B.

* * * * *